(12) United States Patent
Haiges et al.

(10) Patent No.: US 9,964,484 B2
(45) Date of Patent: May 8, 2018

(54) MEASUREMENT DEVICE FOR TESTING HARVESTED GRAIN IN A COMBINE

(71) Applicant: Deere & Company, Moline, IL (US)

(72) Inventors: Wolfram Haiges, Magstadt (DE); Georg Kormann, Zweibruecken (DE)

(73) Assignee: Deere & Company, Moline, IL (US)

( * ) Notice: Subject to any disclaimer, the term of this patent is extended or adjusted under 35 U.S.C. 154(b) by 0 days. days.

(21) Appl. No.: 15/212,488

(22) Filed: Jul. 18, 2016

(65) Prior Publication Data

US 2017/0045444 A1 Feb. 16, 2017

(30) Foreign Application Priority Data

Aug. 11, 2015 (DE) .................. 10 2015 215 299

(51) Int. Cl.
*G01J 5/02* (2006.01)
*G01N 21/359* (2014.01)
*A01D 41/127* (2006.01)
*G01N 21/85* (2006.01)
*G01N 33/10* (2006.01)

(52) U.S. Cl.
CPC ....... *G01N 21/359* (2013.01); *A01D 41/1277* (2013.01); *G01N 21/85* (2013.01); *G01N 33/10* (2013.01); *G01N 2021/8592* (2013.01); *G01N 2201/021* (2013.01)

(58) Field of Classification Search
CPC .. G01N 21/35; G01N 21/359; G01N 21/3504; G01J 3/02; G01J 3/42
See application file for complete search history.

(56) References Cited

U.S. PATENT DOCUMENTS

| 5,092,819 A | 3/1992 | Schroeder et al. |
| 6,327,899 B1 | 12/2001 | Diekhans et al. |
| 6,559,655 B1 * | 5/2003 | Rosenthal ............ G01N 21/359 |
| | | 250/252.1 |

(Continued)

FOREIGN PATENT DOCUMENTS

| DE | 19744485 A1 | 4/1999 |
| DE | 10236515 C1 | 9/2003 |

(Continued)

OTHER PUBLICATIONS

German Search Report in foreign counterpart application 16182935.3, dated Dec. 23, 2016 (4 pages).

*Primary Examiner* — David Porta
*Assistant Examiner* — Mamadou Faye
(74) *Attorney, Agent, or Firm* — Rathe Lindenbaum LLP

(57) ABSTRACT

A grain measurement device (76) comprises a chamber (80) having an inlet (82) and an outlet (84) for grain that is to be tested. A spectrometer is equipped with a light source (89) and a detector (91) for light which was generated by the light source (89) and was transmitted through the sample. The detector (91) is connected to an analyzer (134) for wavelength-resolved analysis of the received light. A mounting (93) of one of the light source (89) or detector (91) can be moved with respect to the other (91, 89 by a drive (106), which moves the mounting (93) for purposes of conveying the sample either in the flow direction (130) or in the opposite direction, in order to break up the sample or to avoid bridging and/or jamming of the sample in the measurement chamber (80).

20 Claims, 4 Drawing Sheets

(56) References Cited

U.S. PATENT DOCUMENTS

2008/0137087 A1* 6/2008 Greten ................. G01N 21/359
356/445
2008/0231853 A1* 9/2008 Berzaghi .............. G01N 21/276
356/326

FOREIGN PATENT DOCUMENTS

| DE | 102010062417 A1 | 6/2011 |
|---|---|---|
| EP | 1639879 A2 | 3/2006 |
| EP | 1894461 A1 | 3/2008 |
| EP | 2119339 A1 | 11/2009 |
| WO | 03029792 A1 | 4/2003 |
| WO | 2007/034530 A2 | 3/2007 |

* cited by examiner

MEASUREMENT DEVICE FOR TESTING HARVESTED GRAIN IN A COMBINE

FIELD OF THE INVENTION

The invention relates generally to agricultural combines. More particularly, it relates to crop measurement devices. Even more particularly it relates to crop measurement devices for testing harvested grain.

BACKGROUND OF THE INVENTION

Within the framework of precision agriculture, there is the need to test harvested product for certain properties while still in the field. For example, the measured values can be electronically plotted to provide a fertilizer application map matched to the product properties or can be used to establish the market price of the harvest or to distribute the harvest into different containers in dependence on quality. In a combine, for example, the moisture content of harvested grain or its protein content can be determined. A measurement method that is available in particular is near infrared spectroscopy, in which a sample of the harvested grain is transported to a measurement chamber by gravity or an attached conveyor and irradiated there with broadband light, the spectrum of which (also) extends into the near infrared region. The light transmitted by or reflected from the sample is acquired by a detector and analyzed by the detector in dependence on wavelength. In this regard, see, for example, DE 10 2010 062 417 A1 and the references cited there.

Since calibration measurements are available from laboratory analyses, transmission measurement is preferred in many cases over a reflection measurement. To be sure, the average free wavelength of light within the grain sample is highly dependent on the harvested product, being, for example, about 9 mm in the case of rapeseed (canola) and about 20 mm for maize or soy. This means that it is advantageous to match the distance between the light source and the detector to the harvested product. For this, it was proposed in the prior art to make two opposite walls of the measurement chamber movable relative to each other and to equip one of the walls with the light source and the other with the detector (U.S. Pat. No. 6,559,655 B1) or to affix the light source to one wall and to mount the detector movably on the opposite wall, so that it can be moved more or less further from its wall into the measurement chamber, either by hand or by means of a motor (for comparison see WO 2007/034530 A2, which is seen as generic).

A problem in testing harvested product in a measurement chamber is that in the chamber the product can form bridges or cause a blockage or jamming there even when the size of the passageway in the measurement chamber (as described in WO 2007/034530 A2) is greater than the distance between the light source and detector is supposed to be. To avoid this problem, in the case of a moisture detector, separate elements were proposed for forced cleaning or emptying of the measurement chamber (DE 197 44 485 A1), which however were quite expensive. The use of the transmission principle, moreover, prevents a conveyor feeding the harvested product to the measurement chamber from extending into the measurement chamber to avoid jamming, since then it would adversely affect the measurement.

The problem underlying the invention will be seen in making available a measurement device that is an improvement over the prior art, and which does not have the said disadvantages or has them to a lesser degree.

SUMMARY OF THE INVENTION

A measurement device for testing harvested grain for a combine comprises a measurement chamber with an inlet and an outlet for a sample of harvested product that is to be tested, where the measurement chamber is designed so that in operation the sample passes along a flow direction from the inlet into the measurement chamber and from there to the outlet. A transmission spectrometer is outfitted with a first element in the form of a light source and a second element having a detector for the light that was generated by the light source and transmitted through the sample. The detector is connected to an analyzer for wavelength-resolved analysis of the received light, and a mounting of one of the elements of the transmission spectrometer can be moved with respect to the other element by a drive motor. The drive motor is set up to move the mounting, in the sense of conveying the sample in the flow direction and/or in the opposite direction in order to break up or to avoid bridging and/or jamming of the sample in the measurement chamber.

In other words, the mounting of one of the elements of the transmission spectrometer is moved by the drive motor not just along the direction of travel of the light, i.e., across the direction of flow of the sample through the measurement chamber, but rather (also or only) along the flow direction, be it in the flow direction or opposite to it or in both of the said directions in succession. The drive motor thus serves not only to position the mounting and thus the element, but also or only to loosen the sample and break up or avoid bridges and/or jamming of the sample in the measurement chamber. The measurement precision is improved in this way and regular monitoring and cleaning of the measurement chamber by the operator becomes unnecessary.

In a possible embodiment, the drive motor is configured to vary the distance between the elements in order to match it to the average wavelength of the light through the sample (which is dependent on the type and especially the color of the sample). The drive motor thus serves to move the element into a position that is suitable for the measurement. In another embodiment, which is discussed below, an additional drive motor is used for this task, while the said drive motor takes on only the moving of the mounting in the flow direction. Mixed embodiment types are also conceivable, where the [one] drive motor and the other drive motor each produces a part of the positioning movement of the mounting in the direction of travel of the light.

According to a first embodiment, a measurement device for testing harvested grain for a combine comprises: a measurement chamber having an inlet and an outlet for a sample of harvested grain that is to be tested, where the measurement chamber is designed so that in operation the sample passes in a flow direction from the inlet into the measurement chamber and from there to the outlet; a transmission spectrometer having a first element in the form of a light source and a second element having a detector for light, which light is generated by the light source and is transmitted through the sample, where the detector is connected to an analyzer for wavelength-resolved analysis of transmitted light received by the detector; a mounting coupled to one of the first element and the second element for relative movement, such that the first element can be moved with respect to the second element, or the second element can be moved with respect to the first element can be moved with respect to the second element; and a drive configured to move the mounting to move at least one of the first element and the second element relative to the other; wherein the drive is further configured to move the mounting to convey the sample in the flow direction or in a direction opposite the flow direction, such that the sample is either broken up, or bridging or jamming of the sample in the measurement chamber is avoided or reduced.

In a second embodiment, the mounting can be moved along a curved track by the drive. The curved track can have any shape, for example circular, elliptical, rectangular, triangular, or linear (i.e., oriented in the flow direction or at an angle to it).

In this embodiment, too, the detector and the drive can be connected to a control device, which can be operated to control the time of recording of the spectrum for purposes of matching to the average wavelength of the light through the sample, in dependence on the position of the mounting along the curved track. Thus, a spectrum is recorded when the mounting, with the one element of the transmission spectrum, is at a suitable distance from the other element of the transmission spectrometer. If the amplitude of the movement of the mounting in the direction of travel of the light is not sufficient for matching to the required wavelengths of the light through the sample, the position of the curved track can alternatively or additionally be moved by means of the additional drive that was already mentioned for matching to the average wavelength of the light through the sample.

The mounting can be bent at a right angle and comprise a first segment, in which the element is disposed, and which extends along the direction of travel of the light, and a second segment running transverse to the first segment and transverse to the flow direction. This segment can also extend through a side wall of the measurement chamber.

In accordance with one aspect of the invention, a measurement device for testing harvested grain for a combine comprises, a measurement chamber having an inlet and an outlet for a sample of harvested grain that is to be tested, where the measurement chamber is designed so that in operation the sample passes in a flow direction from the inlet into the measurement chamber and from there to the outlet; and a transmission spectrometer having a first element in the form of a light source and a second element having a detector for light, which was generated by the light source and was transmitted through the sample, where the detector is connected to an analyzer for wavelength-resolved analysis of transmitted light received by the detector, and a mounting of one of the first element and the second element can be moved with respect to the second element and the first element, respectively, by a drive, wherein the drive is configured to move the mounting for purposes of conveying the sample in the flow direction or in a direction opposite the flow direction, in order to break up or to avoid bridging and/or jamming of the sample in the measurement chamber.

The drive may be configured to vary a distance between the elements in order to match an average wavelength of the light passing through the sample.

The mounting may comprise a substantially flexible wall, on which the element is attached and which can be brought into a peristaltic movement by the drive.

One or more cams may be moved by the drive along a curved track, which runs in part in parallel to the flow direction, fit on the side of the substantially flexible wall that is turned away from the sample.

The analyzer and the drive may be connected by a control device and the control device can be operated to control the time of recording of a spectrum for purposes of matching to the average wavelength of the light through the sample depending upon a position of the cam or cams, or where the position of the curved track for matching to the average wavelength of the light through the sample can be moved by another drive.

The mounting may be movable along a curved track by the drive.

The analyzer and the drive may be connected by a control device and the control device can be operated to control the time of recording of a spectrum for matching an average wavelength of the light passing through the sample in dependence on a position of the mounting along the curved track or where a position of the curved track can be moved by another drive for matching to the average wavelength of the light through the sample.

The mounting may be bent at a right angle and comprises a first segment, in which the element is disposed, and a second segment that runs transverse thereto and transverse to the flow direction.

In another aspect of the invention, a combine having a measurement device in accordance with claim 1 may be provided.

BRIEF DESCRIPTION OF THE DRAWINGS

The drawings show two embodiment examples of the invention, which are described in more detail below.

DETAILED DESCRIPTION OF THE PREFERRED EMBODIMENTS

Figure 1:
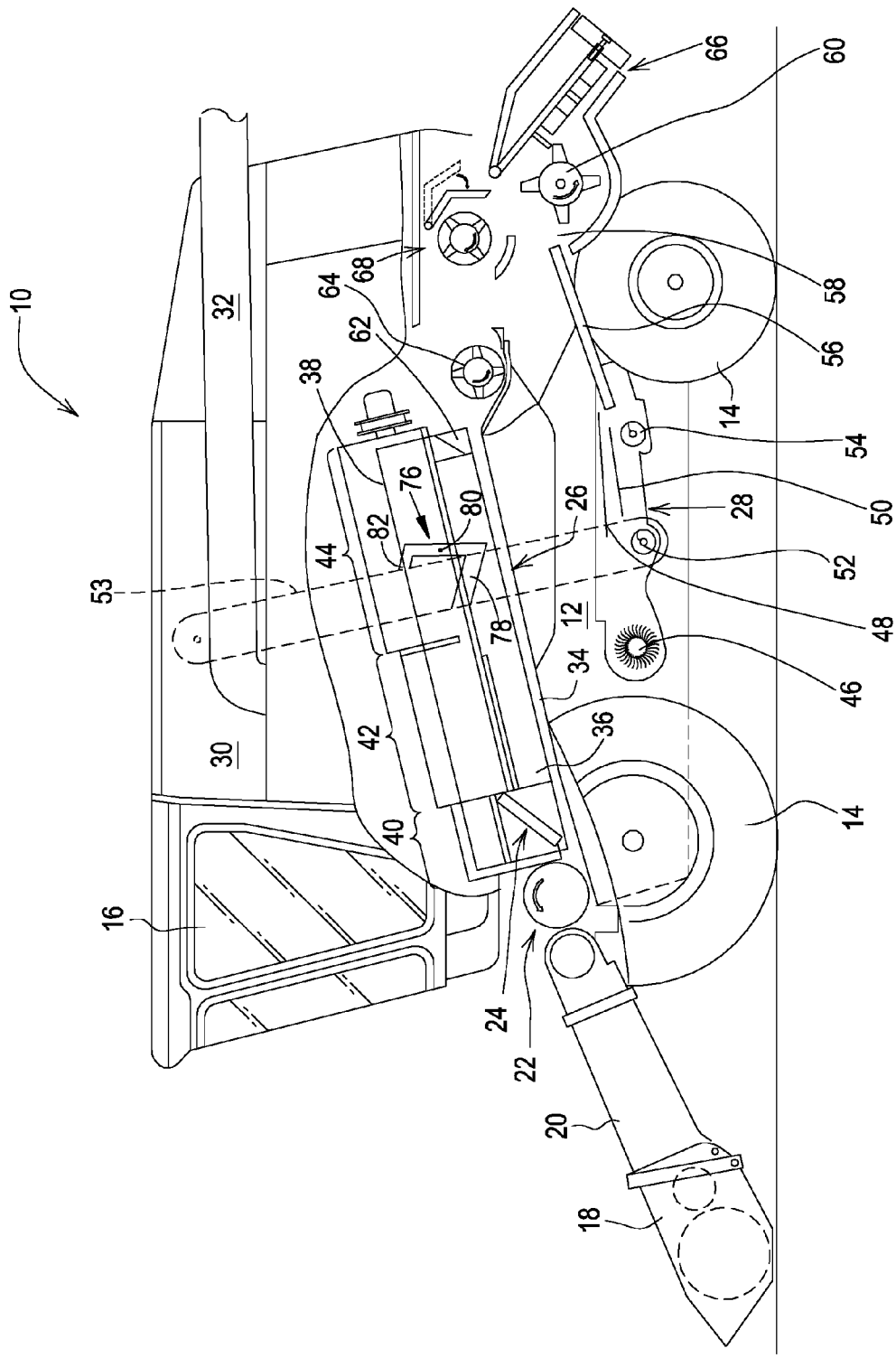
FIG. 1 shows a schematic side view of a combine having a measurement device in accordance with the present invention.

FIG. 1 shows a combine 10 with a supporting frame 12, which rests on front wheels 14 that are driven and rear wheels 14 that are steerable. The operation of the combine 10 is controlled from an operator's cab 16. A cutting mechanism 18 is used to harvest an agricultural grain product and to feed it to an inclined conveyor 20. The harvested product is fed by the inclined conveyor 20 to a guide drum 22. The guide drum 22 guides the harvested product through an inlet transition section 24 to an axial product processing device 26. In the following text, directional data such as forward and backward refer to the forward travel of the combine 10.

The axial product processing device 26 comprises a rotor housing 34 and a rotor 36 disposed therein. The rotor 36 comprises a hollow drum 38, on which the product processing elements for a coating section 40, a threshing section 42, and a cylindrical separating section 44 are affixed. The coating section 40 is disposed on the forward side of the axial product processing device 26. The threshing section 42 and separating section 44 are disposed fore and aft of the coating section 40 in the lengthwise direction. Drum 38 is in the shape of a truncated cone in the coating section 40. The threshing section 42 comprises a truncated cone-shaped forward section and a cylindrical rear section. The separating section 44 of drum 38 is situated at the end of the axial product processing device 26. Instead of an axial product processing device 26, it is also possible to use a tangential threshing drum and an axial separating device or straw walker following it.

Grain and chaff, which fall through a threshing basket associated with the threshing section 42 and a separating grate associated with the separating section 44, are sent to a cleaning system 28 by a blower 46 and to lamellar sieves 48, 50, which can be moved in a swinging motion. The cleaning system 28 removes the chaff and sends the clean grain through an auger conveyor 52 to a grain elevator 53. The grain elevator 53 drops the clean grain into a grain tank 30. The clean grain in grain tank 30 can be unloaded by an unloader auger 32 to a grain car, trailer, or truck. Agricultural product remaining at the rear end of the bottom lamellar sieve 50 is sent back to the axial product processing device 26 or to a separate secondary thresher (not shown) by means of an auger 54 and a return conveyor (not shown). The agricultural product remnant at the rear end of the upper lamellar sieve 48, which essentially consists of waste (chaff) and small straw pieces, is sent rearward to an inlet 58 of a straw chopper 60 by an oscillating floor conveyor 56.

Threshed straw leaving the separating section 44 is expelled from the axial product processing device 26 through an outlet 62 and sent to a discharge drum 64. The discharge drum 64 discharges the straw to the rear. To the rear of the discharge drum 64 and about the vertical height of its axis of rotation is an overshot drum conveyor 68, which either ejects the straw to the rear (swath deposit) or sends it to the straw chopper 60, which sends the chopped straw to an active distributor 66.

Figure 2:
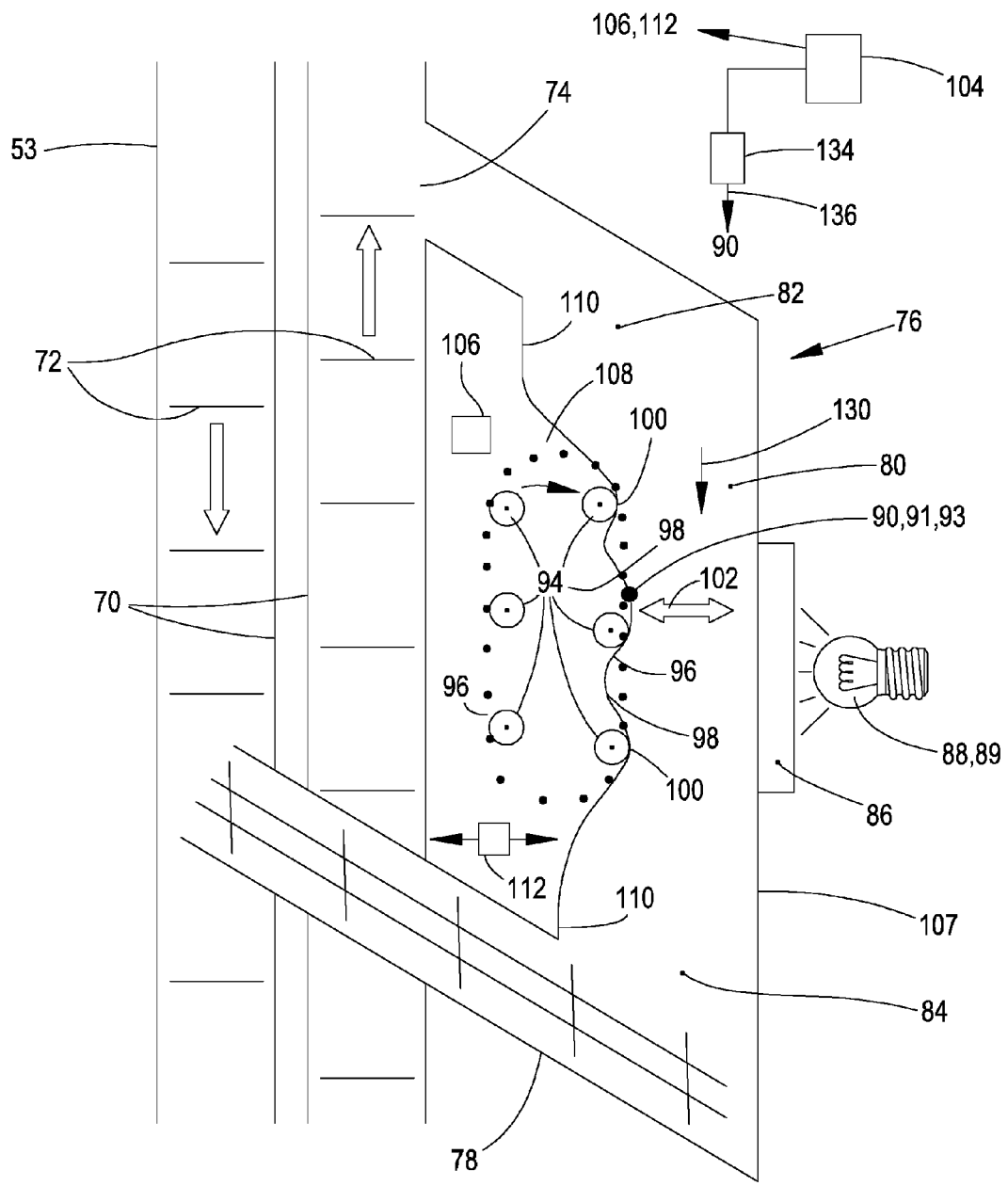
FIG. 2 shows a schematic side view of a first embodiment of the measurement device of FIG. 1.

As shown in FIG. 2, the grain elevator 53 is made as a paddle conveyor. Paddles 72 are mounted at regular distances on a powered drive mechanism 70 in the form of a chain or the like that runs around a lower and an upper pulley. The ascending leg of the conveyor carries the clean grain up. An opening 74, through which a sample of the grain can travel into a measurement device 76, in which the sample can be tested by a transmission spectrometer for its constituents such as water, protein, etc., is provided in the side wall of the grain elevator 53. The sample is then carried by a conveyor 78 to the ascending or descending leg of the grain elevator 53. The measurement device 76 could also be mounted at any other point on the combine 10 at which clean grain can be withdrawn, for instance at auger conveyor 52 or at the outlet of the grain elevator 53, or at any point of a grain tank filler auger (not shown).

The measurement device 76 comprises a measurement chamber 80 with an upper inlet 82, through which the sample travels into the measurement chamber 80 continuously (or gradually, for example, using an upper inlet door, not shown). In operation the sample flows downward through the measurement chamber 80 in a flow direction 130 and arrives at a lower outlet 84, from which it is again transported by the conveyor 78. A transmission spectrometer operating in the near infrared range, which has a first element 88 in the form of a light source 89 (for example, a halogen lamp or an LED structure), which illuminates the inside space of the measurement chamber 80 through a window pane 86, is mounted in the measurement chamber 80. The transmission spectrometer additionally comprises a second element 90 in the form of a detector 91 for the light that was transmitted (passed) through the sample contained in the measurement chamber 80. The detector 91 could comprise a window pane and/or gathering lens and guide the light to an analyzer 134, which resolves the light by wavelength and determines the intensities of the wavelengths, in which regard one is referred to the prior art according to U.S. Pat. No. 5,751,421 A, DE 199 22 867 A1, WO 2007/034530 A2, DE 10 2010 062 417 A1, and DE 10 2011 054 841 A1, the disclosure of which is incorporated into these documents by reference. An electronic control device 104 determines the content of the said constituents in the sample in a substantially known way by means of calibration data and the measured wavelength-dependent intensities. The analyzer 134 can spatially be directly adjacent to the detector 91 or integrated therein or be disposed at a distance therefrom and thus connected by a light guide 136.

While the wall 107, to which the first element 88 and the window pane 86 are affixed, is substantially rigid, the opposite wall 108 of the measurement chamber 80 consists of a substantially flexible material such as rubber or plastic. The second element 90 is affixed to this wall 108 of substantially flexible material and moves with the wall 108 when it is set into a peristaltic motion by cams 94, which are continuously moved by a drive 106 along a curved track 96, during which parts of the wall 108 are gradually pushed outward by the cams 94 and form crests 100, while wall 108 forms valleys 98 in between due to the pressure of the sample. The curved track 96 in the embodiment that is shown is somewhat elliptical, but it could also have the form of a stadium track with straight vertical segments connected by semicircles, or any other shape. Above and below the measurement chamber 80, wall 108 transitions into rigid walls 110 or is connected to such walls.

The mounting 93 for the second element 90 that is formed by wall 108 thus is moved by drive 106 continuously in the direction of arrow 102, toward the first element 88 and back. In addition, the said mounting 93 is moved for purposes of conveying the sample through the measurement chamber 80 in the flow direction 130, which breaks up the sample or avoids bridging and/or jamming of the sample in the measurement chamber 80. The movement of wall 108 can serve to trigger a measurement by the transmission spectrometer when the elements 88 and 90 are at a distance from each other that is suitably matched to the wavelength of the light through the sample via the control device 104, which knows the position of the drive 106 and thus the cam 94 through an appropriate detector and/or the control means of the drive 106, which is designed as a step motor or servomotor. If the amplitude of the movement of the second element 90 is not sufficient for this, the control device 104 can cause an additional drive 112 if necessary to move the entire curved track 96 (and with it cams 94 and thus also wall 108) in the direction of arrow 102 by an additional drive 112. Of course, the first element 88 could also be mounted on wall 108, while the second element 90 then is affixed to the solid wall 107.

Figure 3:
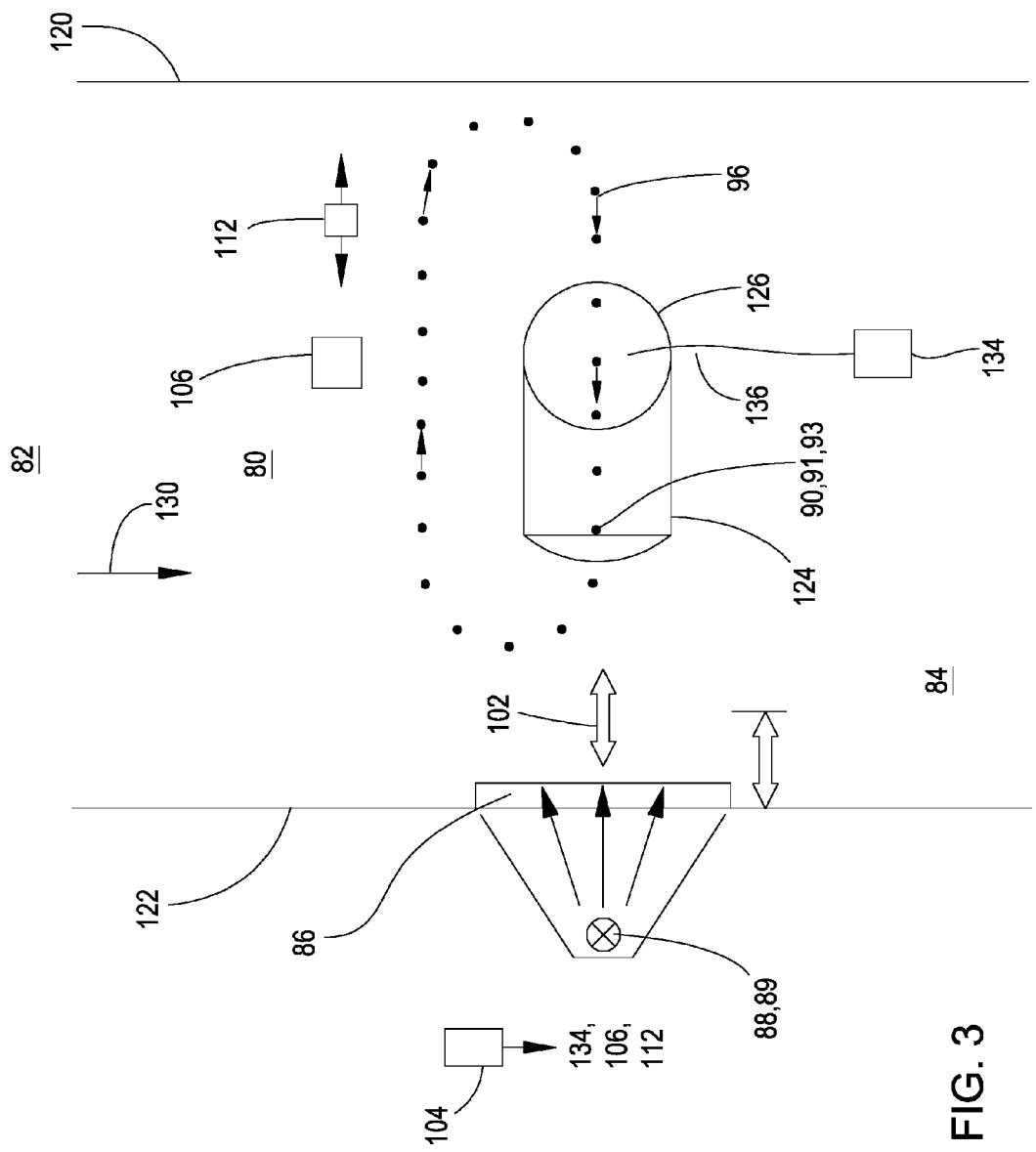
FIG. 3 shows a schematic side view of a second embodiment of the measurement device of FIG. 1.
Figure 4:
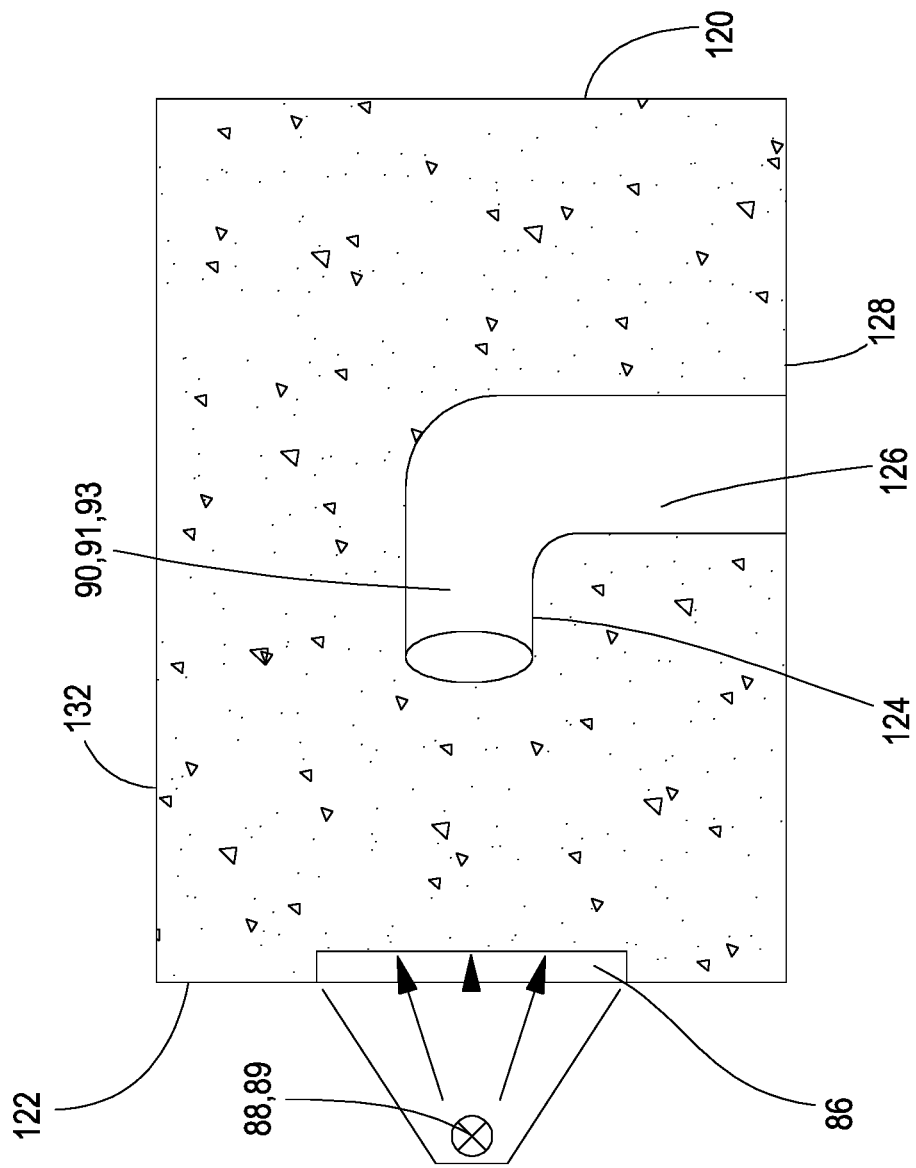
FIG. 4 shows a top view of the measurement device of FIG. 3.

In the case of the second embodiment shown in FIGS. 3 and 4, in which elements corresponding with the first embodiment have the same reference numbers, the entire second element 90 with its mounting 93 moves on a curved track 96, which is also nearly elliptical and in part extends along the arrow 102 representing the direction of travel of the light from the first element 88 to the second element 90 and in part runs transverse to it, i.e., against the flow direction 130 of the sample of agricultural product through the measurement chamber 80, which in FIG. 3 runs from top down and in FIG. 4 runs perpendicular to the viewing plane. The second element 90 of the transmission spectrometer thus moves not only in the direction of travel of the light (arrow 102), but also (at the left hand reversal point in FIG. 3) against the flow direction 130 and (at the right hand reversal point in FIG. 3) in the flow direction 130, which loosens the sample and avoids jamming and bridging. The direction of rotation of mounting 93 can also be reversed in FIG. 3.

As with the first embodiment, the control device 104, for which the position of the drive 106 and thus cams 94 is known via an appropriate detector and/or by the control of drive 106, which is designed as, for example, a step motor or servomotor, can then trigger a measurement by the transmission spectrometer exactly when the elements 88 and 90 are at a suitable distance from each other that is matched to the wavelength of the light through the sample. If the amplitude of the movement of the second element 90 along the curved track 96 (i.e., along arrow 102) is not sufficient for this, the control device 104 can trigger an additional drive 112, if necessary, to move the entire curved track 96 (and with it the second element 90) by another drive 112 in the direction of arrow 102. Of course, the first element 88 could be moved along the curved track 96, while the second element 90 would then be rigidly affixed to the solid wall 122.

The second element 90 is substantially bent at a right angle and has a first segment 124, which extends along arrow 102, and a second segment 126, which is perpendicular thereto and extends in the flow direction 130. The second segment 126 extends through a side wall 128 of the measurement chamber 80, which lies opposite a fourth wall 132.

The claims define the invention. The examples illustrated and described in this document show just a few of the ways in which the invention may be made and used.

The invention claimed is:

1. A measurement device for testing harvested grain for a combine, comprising:
    a measurement chamber having an inlet and an outlet for a sample of harvested grain that is to be tested, where the measurement chamber is designed so that in operation the sample passes in a flow direction from the inlet into the measurement chamber and from there to the outlet;
    a transmission spectrometer having a first element in the form of a light source and a second element having a detector for light, which light is generated by the light source and is transmitted through the sample, where the detector is connected to an analyzer for wavelength-resolved analysis of transmitted light received by the detector;
    a mounting coupled to one of the first element and the second element for relative movement, such that the first element can be moved with respect to the second element, or the second element can be moved with respect to the first element, wherein the mounting comprises a grain contact surface to contact grain within the chamber, the grain contact surface being movable in the flow direction or opposite the flow direction, wherein the grain contact surface is movable in a direction parallel to the flow direction; and
    a drive configured to move the mounting to move at least one of the first element and the second element relative to the other;
    wherein the drive is further configured to move the mounting to move the grain contact surface in the flow direction or opposite the flow direction to convey the sample in the flow direction or in a direction opposite the flow direction, such that the sample is either broken up, or bridging or jamming of the sample in the measurement chamber is avoided or reduced.

2. The measurement device according to claim 1, where the drive is configured to vary a distance between the elements in order to match an average wavelength of the light passing through the sample.

3. The measurement device according to claim 2, where the mounting comprises a flexible wall, on which the element is attached and which can be brought into a peristaltic movement by the drive, the flexible wall having a portion forming the grain contact surface.

4. The measurement device according to claim 3, where one or more cams, which can be moved by the drive along a curved track, which runs in part in parallel to the flow direction, fit on the side of the flexible wall that is turned away from the sample.

5. The measurement device according to claim 4, where the analyzer and the drive are connected by a control device and the control device can be operated to control the time of recording of a spectrum for purposes of matching to the average wavelength of the light through the sample depending upon a position of the cam or cams, or where the position of the curved track for matching to the average wavelength of the light through the sample can be moved by another drive.

6. The measurement device according to claim 1, where the mounting and the grain contact surface are movable along a curved track by the drive.

7. The measurement device according to claim 6, where the analyzer and the drive are connected by a control device and the control device can be operated to control the time of recording of a spectrum for matching an average wavelength of the light passing through the sample depending upon a position of the mounting along the curved track or where a position of the curved track can be moved by another drive for matching to the average wavelength of the light through the sample.

8. The measurement device according to claim 7, where the mounting is bent at a right angle and comprises a first segment, in which one of the first element and the second element is disposed, and a second segment that runs transverse thereto and transverse to the flow direction.

9. A combine having a measurement device in accordance with claim 1.

10. The measurement device of claim 1, wherein the grain contact surface is within the chamber and movable along a continuous loop.

11. The measurement device of claim 1, wherein the grain contact surface is movable in a direction oblique to the flow direction.

12. A measurement device for grain, the measurement device comprising:
    a measurement chamber having an inlet and an outlet for a sample of grain to be tested, wherein the sample of grain is to pass from the inlet to the outlet in a flow direction;
    a sensor element;
    a grain contact surface coupled to the sensor element to move with movement of the sensor element, the grain contact surface extending oblique to the flow direction within the measurement chamber; and
    a drive coupled to the grain contact surface to concurrently move the grain contact surface and the sensor element so as to move the sample of grain non-perpendicular to the flow direction such that the sample is either broken up, or bridging or jamming of the sample in the measurement chamber is avoided or reduced.

13. The measurement device of claim 12, wherein the grain contact surface is movable along a continuous loop path within the measurement chamber.

14. The measurement device of claim 12 further comprising a flexible wall, at least a portion of which provides the grain contact surface.

15. The measurement device of claim 14, wherein the drive is configured to peristaltically the flexible wall.

16. The measurement device of claim 12, wherein the sensor element comprises one of a light emitter and a light sensor.

17. A measurement device for testing harvested grain for a combine, comprising:
- a measurement chamber having an inlet and an outlet for a sample of harvested grain that is to be tested, where the measurement chamber is designed so that in operation the sample passes in a flow direction from the inlet into the measurement chamber and from there to the outlet;
- a transmission spectrometer having a first element in the form of a light source and a second element having a detector for light, which light is generated by the light source and is transmitted through the sample, where the detector is connected to an analyzer for wavelength-resolved analysis of transmitted light received by the detector;
- a mounting coupled to one of the first element and the second element for relative movement, such that the first element can be moved with respect to the second element, or the second element can be moved with respect to the first element; and
- a drive configured to move the mounting to move at least one of the first element and the second element relative to the other;
- wherein the drive is further configured to move the mounting to convey the sample in the flow direction or in a direction opposite the flow direction, such that the sample is either broken up, or bridging or jamming of the sample in the measurement chamber is avoided or reduced, where the mounting comprises a flexible wall, on which the element is attached and which can be brought into a peristaltic movement by the drive.

18. The measurement device according to claim 10, where one or more cams, which can be moved by the drive along a curved track, which runs in part in parallel to the flow direction, fit on the side of the flexible wall that is turned away from the sample.

19. The measurement device according to claim 11, where the analyzer and the drive are connected by a control device and the control device can be operated to control the time of recording of a spectrum for purposes of matching to the average wavelength of the light through the sample depending upon a position of the cam or cams, or where the position of the curved track for matching to the average wavelength of the light through the sample can be moved by another drive.

20. A measurement device for testing harvested grain for a combine, comprising:
- a measurement chamber having an inlet and an outlet for a sample of harvested grain that is to be tested, where the measurement chamber is designed so that in operation the sample passes in a flow direction from the inlet into the measurement chamber and from there to the outlet;
- a transmission spectrometer having a first element in the form of a light source and a second element having a detector for light, which light is generated by the light source and is transmitted through the sample, where the detector is connected to an analyzer for wavelength-resolved analysis of transmitted light received by the detector;
- a mounting coupled to one of the first element and the second element for relative movement, such that the first element can be moved with respect to the second element, or the second element can be moved with respect to the first element, wherein the mounting comprises a grain contact surface to contact grain within the chamber, the grain contact surface being movable in the flow direction or opposite the flow direction, wherein the grain contact surface is movable in a direction oblique to the flow direction; and
- a drive configured to move the mounting to move at least one of the first element and the second element relative to the other;
- wherein the drive is further configured to move the mounting to move the grain contact surface in the flow direction or opposite the flow direction to convey the sample in the flow direction or in a direction opposite the flow direction, such that the sample is either broken up, or bridging or jamming of the sample in the measurement chamber is avoided or reduced.

* * * * *